United States Patent [19]

Watson et al.

[11] Patent Number: 4,965,386

[45] Date of Patent: Oct. 23, 1990

[54] HYDROSILATION, AND DEHYDROCONDENSATION OF SILICON HYDRIDES, CATALYZED BY SCANDIUM, YTTRIUM AND RARE EARTH METAL COMPOUNDS

[75] Inventors: Patricia L. Watson, Wilmington; Frederick N. Tebbe, Hockessin, both of Del.

[73] Assignee: E. I. Du Pont de Nemours and Company, Wilmington, Del.

[21] Appl. No.: 498,937

[22] Filed: Mar. 26, 1990

[51] Int. Cl.$^5$ .............................................. C07F 7/08
[52] U.S. Cl. .................................... 556/430; 556/479; 423/347
[58] Field of Search ................ 556/430, 479; 423/347

[56] References Cited

U.S. PATENT DOCUMENTS 4,450,283  5/1984  McAfee et al. ...................... 556/479
4,537,942  8/1985  Brown-Wensley et al. ... 556/430 X

FOREIGN PATENT DOCUMENTS 314327  5/1989  European Pat. Off. .
2565234  6/1984  France .

OTHER PUBLICATIONS

H. Woo and T. D. Tilley, J. Am. Chem. Soc., vol. 111, pp. 8043-8044 (1989).
Claire Aitken et al., J. Organometal. Chem., vol. 279, pp. C11-C13 (1985).
Claire Aitken et al., J. Am. Chem. Soc., vol. 108, pp. 4059-4066 (1986).
J. F. Harrod et al., Organometallics, vol. 6, pp. 1381-1387 (1987).
J. F. Harrod, Polym. Prepr., vol. 28, pp. 403-404 (1987).
Clare Aitken et al., Can. J. Chem., vol. 64, pp. 1677-1679 (1986).
C. Aitken et al., Can. J. Chem., vol. 65, pp. 1804-1809 (1987).
W. H. Campbell et al., Organometallics, vol. 8, pp. 2615-2618 (1989).
M. G. Voronkov and S. P. Sushchinskaya, Zh. Obshch. Khim., vol. 56, pp. 627-632 (1986).

*Primary Examiner*—Paul F. Shaver

[57] ABSTRACT

A process for forming polysilanes from silicon hydrides by contacting the silicon hydride with catalytic amounts of selected scandium, yttrium and rare earth metal hydrides, and a process for hydrosilation of alpha-olefins in which an alpha-olefin is contacted with a silicon hydride in the presence of catalytic amounts of selected scandium, yttrium and rare earth metal compounds.

43 Claims, No Drawings

HYDROSILATION, AND DEHYDROCONDENSATION OF SILICON HYDRIDES, CATALYZED BY SCANDIUM, YTTRIUM AND RARE EARTH METAL COMPOUNDS

FIELD OF INVENTION

Processes for the production of polysilanes, useful as precursors of silicon carbide, and for the hydrosilation of alpha-olefins, which products are useful as chemical intermediates, are provided.

BACKGROUND OF THE INVENTION

H. Woo and T. D. Tilley, J. Am. Chem. Soc., vol. 111 pp. 8043-8044 (1989) describe the dehydrocondensation of silanes of the type $RSiH_3$ with dimethylbis(pentamethylcyclopentadienyl) compounds of zirconium and hafnium to form polysilanes. Other isoluble hafnium and zirconium compounds which were postulated to be intermediates in the dehydrocondensation reaction were also shown to be active in forming the polysilanes.

French Patent No. 2,565,234 reports the dehydrocondensation of silanes of the formula $RSiH_3$ with similar (to those above) compounds of titanium and zirconium. The products of the reactions are polysilanes. J. F. Harrod and coworkers, in a series of papers, expanded on this reaction: J. Organometal. Chem., vol. 279, pp. C11-13 (1985); J. Am. Chem. Soc., vol. 108, pp. 4059-4066 (1986); Organometallics, vol. 6, pp. 1381-1387 (1987); Polym. Prepr. vol. 28 pp. 403-404 (1987); Can. J. Chem., vol. 64, pp. 1677-1679 (1986); and Can. J. Chem., vol. 65 pp. 1804-1809 (1987). These papers disclose reactions to form the polysilanes and the structure of the polysilanes so produced. The polysilanes are described as being of relatively low molecular weight, and containing up to about 20 silicon atoms. W. H. Campbell, et. al., Organometallics, vol. 8 pp. 2615-2618 (1989) further investigated the products of the reaction of bis ($\eta^5$-cyclopentadienyl)dimethylzirconium with n-butylsilane. Cyclic and linear polysilanes containing up to 8 silicon atoms were obtained.

European Patent Application No. 314,327 describes the polymerization of compounds of the formula $R^1R^2SiH_2$, where $R^1$ is hydrogen or hydrocarbon and $R^2$ is hydrocarbon, using an organometallic complex of nickel, cobalt, ruthenium, palladium or iridium as a catalyst.

In all of the above references no mention is made of the use of scandium, yttrium or rare earth metal compounds to catalyze the dehydrocondensation of silanes to form polysilanes.

Hydrosilation of olefins, particularly alphaolefins, is a well known reaction. Such reactions are known to be catalyzed by a variety of agents, including certain transition metals, see for example E. Y. Lukevits and M. G. Voronkov, Organic Insertion Reactions of Group IV Elements, Consultants Bureau, New York, 1966.

M. G. Voronkov and S. P. Sushchinskaya, Zh. Obshch. Khim., vol. 56, pp. 627-32 (1986) describe the use of $LaCl_3$, $CeCl_3$, $NdCl_3$, $EuCl_3$, $DyCl_3$, $ErCl_3$ and $LuCl_3$ as additives for the $H_2PtCl_6$ catalyzed hydrosilation of phenylacetylene with triethylsilane. Several of these metal halides increased the yield and/or changed the ratio of isomers obtained when compared with the reaction using $H_2PtCl_6$ alone. No reactions were run without $H_2PtCl_6$, a known hydrosilation catalyst.

It is the object of this invention to provide processes for the hydrosilation of alpha-olefins, and the dehydrocondensation of silanes of the type $R^1R_8SiH_2$ to form polysilanes. It is a further object of this invention to provide novel catalysts for use in these processes.

SUMMARY OF THE INVENTION

A process is provided for the hydrosilation of alpha-olefins comprising contacting a selected silane containing a hydrogen bound to silicon with an alphaolefin in the presence of a catalyst of the formula $Cp_2MR^2$, wherein Cp is $\eta^5$-cyclopentadienyl optionally substituted with hydrocarbyl, substituted hydrocarbyl and silyl, M is scandium, yttrium or a rare earth metal, and $R^2$ is hydrocarbyl, hydrogen, substituted hydrocarbyl and silyl. Also provided is a process for the production of polysilanes, comprising contacting a silane of the formula $R^1R_8SiH_2$ with a compound of the formula $Cp_2MR^2$, wherein $R^1$ is selected hydrocarbyl, $R_8$ is hydrogen or selected hydrocarbyl and Cp, M and $R^2$ are as defined above.

DETAILS OF THE INVENTION

This invention comprises processes for forming polysilanes from silicon hydrides and for hydrosilation of alpha-olefins using a scandium, yttrium or rare earth metal compound as a catalyst. The products of the hydrosilation reaction are useful as chemical intermediates, adhesion promoters, solvents, etc. The polysilanes are useful as intermediates in the preparation of silicon carbide, as photoresist materials, and photopolymerization catalysts.

This invention concerns a process for the production of polysilanes, comprising, contacting a silane of the formula $R^1R_8SiH_2$ with a compound of the formula $Cp_2MR^2$, wherein:

$R^1$ is hydrogen, saturated hydrocarbyl or aromatic hydrocarbyl;

$R^8$ is hydrogen, saturated hydrocarbyl or aromatic hydrocarbyl;

Cp is $\eta^5$-cyclopentadienyl, optionally substituted with hydrocarbyl, substituted hydrocarbyl and silyl;

M is scandium, yttrium or a rare earth metal; and $R^2$ is saturated or aromatic hydrocarbyl, substituted saturated or aromatic hydrocarbyl, hydrogen or silyl.

By the term "substituted hydrocarbyl" is meant herein that the hydrocarbyl group may contain substituents that do not interfere with the process being described, and do not render the subject scandium, yttrium or rare earth metal compound unstable. Examples of such substituents include but are not limited to t-butoxy and N,N-dimethylamino. By the term "silyl" is meant the group $-SiH_3$ wherein the hydrogen atoms may be substituted by hydrocarbyl groups.

"Polysilanes" are compounds containing one or more silicon-silicon bonds. The present process may be used to prepare disilanes, trisilanes, tetrasilanes, etc., if the process is stopped relatively soon after the reaction is initiated. However, a mixture of polysilanes, including disilanes, will usually result from such a reaction.

For the silane of formula $R^1R_8SiH_2$, preferred $R^1$ groups are alkyl and aryl. Especially preferred $R^1$ groups are alkyl containing less than 6 carbon atoms and aryl. Most preferred $R^1$ groups are methyl, ethyl and phenyl.

Preferred $R^8$ groups are hydrogen, alkyl and aryl. Especially preferred $R_8$ groups are hydrogen, alkyl containing less than 6 carbon atoms and aryl. Most preferred $R^8$ groups are hydrogen, methyl and phenyl.

For the compound of formula $Cp_2MR^2$, preferred $R^2$ groups are hydrogen, alkyl and phenyl. Especially preferred $R^2$ groups are hydrogen and alkyl groups containing less than 6 carbon atoms. A most preferred alkyl group is methyl. Another preferred $R^2$ group is one that is substituted with one or more silicon atoms on the carbon atom bound to the metal. Thus another especially preferred $R^2$ group is bis(trimethylsilyl)methyl.

Preferred Cp groups are $\eta^5$-cyclopentadienyl and $\eta^5$-pentamethylcyclopentadienyl.

Rare earth metals are those metals with atomic numbers of 57 through 71, namely lanthanum, cerium, praseodymium, neodymium, promethium, samarium, europium, gadolinium, terbium, dysprosium, holmium, erbium, thulium, ytterbium and lutetium. Preferred metals (M) are yttrium, lanthanum, samarium and lutetium. An especially preferred metal is lutetium.

The molar ratio of $R^1R^8SiH_2$ to scandium, yttrium or rare earth metal compound is from about 30:1 to about 10,000:1, preferably from about 100:1 to about 1,000:1.

A solvent may be used, but is not necessary. Any solvent employed should not decompose the starting materials or products, or interfere with the reaction. Preferred solvents are saturated hydrocarbons or aromatic hydrocarbons. Especially preferred solvents are alkanes, cycloalkanes and aromatic hydrocarbons.

The reaction usually may be run from a few hours to a few days. It is believed that the molecular weight of the product polysilane generally increases with time (as evidenced by the increasing viscosity of the reaction mass).

The process is usually run at ambient pressure, but elevated pressures above normal atmospheric may be used when one of the starting materials, for example methylsilane, is relatively volatile. Oxygen and water should be excluded to avoid destruction of starting materials and/or products. It is convenient to use a vacuum or an inert atmosphere such as nitrogen or argon to exclude moisture and oxygen. The starting materials should be dry and oxygen free.

The process may be run at temperatures of from about $-30°$ C. to about $250°$ C., preferably from about $0°$ C. to about $150°$ C.

It is preferred if the reaction mass is agitated. Care should be taken that the gas formed in the reaction (principally hydrogen) can be adequately vented, and that any foaming can be controlled, so as to not lose product or cause a hazard. Product may be isolated by methods well known to those skilled in the art, such as evaporation of solvent. Another object of this invention is to provide a process for the hydrosilation of alpha-olefins, comprising, contacting an alpha-olefin of the formula $H_2C=CR^3R^4$ with a silane of the formula $R^5R^6SiH_2$ in the presence of a catalyst of the formula $Cp_2MR^2$, wherein:

$R^3$ and $R^4$ are independently hydrocarbyl or substituted hydrocarbyl;

$R^5$ is hydrogen, hydrocarbyl or substituted hydrocarbyl;

$R^6$ is hydrogen, siloxy, hydrocarbyl or substituted hydrocarbyl;

Cp is $\eta^5$-cyclopentadienyl, or $\eta^5$-cyclopentadienyl substituted with hydrocarbyl, substituted hydrocarbyl or silyl;

M is scandium, yttrium or a rare earth metal; and $R^2$ is saturated or aromatic hydrocarbyl, substituted saturated or substituted aromatic hydrocarbyl, hydrogen or silyl.

The term "substituted hydrocarbyl" is as defined above. Rare earth metals are as defined above. Preferred rare earth metals are yttrium, lanthanum, samarium and lutetium. Lutetium is an especially preferred metal.

For the catalyst of formula $Cp_2MR^2$, preferred $R^2$ groups are hydrogen, alkyl and phenyl. Especially preferred $R^2$ groups are hydrogen and alkyl groups containing less than 6 carbon atoms. A most preferred alkyl group is methyl. Another preferred $R^2$ group is one that is substituted with one or more silicon atoms on the carbon atom bound to the metal. Thus another especially preferred $R^2$ group is bis(trimethylsilyl)methyl.

Preferred Cp groups are $\eta^5$-cyclopentadienyl and $\eta^5$-pentamethylcyclopentadienyl.

In preferred alpha-olefins of formula $H_2C=CR^3R^4$, $R^3$ is hydrogen and $R^4$ is alkyl, or $R^3$ and $R^4$ are both alkyl. As is well known to those skilled in the art, hydrosilation reactions are sensitive to steric hinderance, so that highly hindered olefins may be relatively unreactive. Such hindered olefins will be recognized by those skilled in the art.

In the silane $R^5R^6SiH_2$ the silicon may be part of a disiloxane, trisiloxane or polysiloxane. The silane may also contain more than one silicon atom containing a silicon-hydrogen bond, in which case more than one of the silicon hydrogen bonds per silane molecule may participate in the hydrosilation reaction, depending upon the relative reactivities of the various silicon-hydrogen bonds, and the molar ratio of silane to alpha-olefin used. Normally one mole of alpha-olefin will be present for each mole of silicon-hydrogen bonds that is to take part in the hydrosilation reaction. In the silane $R^5R^6SiH_2$ preferred combinations of $R^5$ and $R^6$ are: $R^5$ is hydrocarbyl and $R^6$ is hydrogen; $R^5$ is hydrocarbyl, and $R^6$ is the same as $R^5$. Preferred hydrocarbyl groups for $R^5$ and $R^6$ are methyl and phenyl. Especially preferred silanes are phenylsilane, methylsilane, dimethylsilane and phenylmethylsilane.

In the hydrosilation reaction, as is well known to those skilled in the art, the Si-H group adds across the double bond of the olefin or substituted olefin to give an alkyl substituted silane. Normally the silicon atom becomes bonded to the terminal carbon atom of the olefinic group. It is also known that sometimes rearrangements of the olefin occur if a polyolefin is used. Internal olefins often isomerize to alpha-olefins under the hydrosilation process conditions, and are then hydrosilated. Such hydrosilations of olefins that have been isomerized to alpha-olefins are also contemplated by the present process. Normally all alpha-olefin groups in a molecule will be hydrosilated, and such "polyalpha-olefins" may be used in this process.

The molar ratio of $R^5R^6SiH_2$ to scandium, yttrium or rare earth metal compound is from about 30:1 to about 10,000:1, preferably from about 100:1 to about 1,000:1.

A solvent may be used, but is not necessary. The solvent should not decompose the starting materials or products, or interfere with the reaction. Preferred solvents are saturated hydrocarbons or aromatic hydrocarbons. Especially preferred solvents are alkanes, cycloalkanes and aromatic hydrocarbons.

The process is usually run at ambient pressure, but pressures above normal atmospheric may be used, for example, when one of the starting materials, for example methylsilane, is relatively volatile. Oxygen and water should be excluded to avoid destruction of starting materials and/or products. It is convenient to use a vacuum or an inert atmosphere such as nitrogen or argon to exclude moisture and oxygen. The starting materials should be dry and oxygen free. The process may be run at temperatures of from about −70° C. to about 250° C., preferably from about −50° C. to about 150° C., and most preferably from about 0° C. to about 100° C.

It is preferred that the reaction mass be agitated. Product may be isolated by methods well known to those skilled in the art, such as passage over a silica gel column to remove catalyst residues, and then distillation.

Although the ingredients may be mixed in any order, it is preferred if the olefin and silane are mixed first. This is to avoid the dehydrocondensation reaction.

In the following Examples, Cp*$_2$LuMe was made by methods described in: P. L. Watson, and G. W. Parshall, Acc. Chem. Res. vol. 18, pp. 51–56, (1985); P. L. Watson, and T. Herskovitz, in Initiation of Polymerization, ACS Symp. Ser., vol. 212, pp. 459–479 (1983); and P. L. Watson J. Chem. Soc. Chem. Commun., vol. 1983, pp. 276–277, each herein incorporated by reference. Cp*$_2$MCH(SiMe$_3$)$_2$ (M=Y, La, Sm) were made by methods described in: Int. Patent Appln. WO 86/5788 A1; and K. H. DenHaan, et. al., Organometallics, vol. 5 pp. 1726–1733 (1986), each herein incorporated by reference.

In the following Examples, the following abbreviations are used:
Cp*—$\eta^5$-pentamethylcyclopentadienyl
GC—gas chromatography
GPC—gel permeation chromatography
Me—methyl
Mn—number average molecular weight
MS—mass spectroscopy
Mw—weight average molecular weight
NMR—nuclear magnetic resonance spectroscopy
Ph—phenyl
THF—tetrahydrofuran Although preferred embodiments of the invention are described hereinafter, it is to be understood that there is no intention to limit the invention to the precise constructions herein disclosed, and it is to be further understood that the right is reserved to all changes coming within the scope of the invention as defined by the appended claims.

EXAMPLE 1

To allow escape of hydrogen from the system, the experiment was conducted in a vessel under a very slow purge of dry nitrogen gas. Phenylsilane, PhSiH$_3$, 500 mg (46 mmol) was added to a solution of Cp*$_2$LuMe, 40 mg (0.087 mmol) in 2 ml of cyclohexane. Effervescence of the solution commenced immediately as gases formed. Subsequently slower evolution of gas occurred over 2 days, and the solution became viscous as H(PhSiH)$_n$H was produced. Solvent was evaporated under vacuum leaving a pale yellow viscous oil. $^1$H NMR spectra of the product in deuterocyclohexane (C$_6$D$_{12}$) contained SiH resonances at $\delta$~4.5–4.8 and ~5.1; and C$_6$H$_5$ resonances at ~7.0 and 7.55. The ratio of SiH to C$_6$H$_5$ resonances was 1:5.2. NMR spectra were similar to those reported for oligomers of H(PhSiH)$_n$H. [C. Aitken; J. F. Harrod ; U. S. Gill, Can. J. Chem., 1987, 65, 1804–1809.]

A portion of the oligomers was heated in a thermal gravimetric analysis instrument under nitrogen at a rate of 5° C./min from ambient temperature to 800° C. Loss of weight (52%) occurred over the temperature range of about 60° C. to 540° C.

EXAMPLE 2

PhSiH$_3$, 149 mg (1.38 mmol) and Cp*$_2$LuMe, 29 mg (0.063 mmol), and dodecane solvent, 26 ml, were combined in an evacuated reaction vessel. The reaction mixture was stirred at ambient temperature. Periodically the mixture was cooled to the temperature of liquid nitrogen, and product gases not condensible at this temperature were collected, measured, and analyzed. The results are summarized in the table below. Gases obtained during the first two and during the last two reaction periods were combined for analysis by gas chromatography-mass spectroscopy (GC/MS).

| Gas Sample | Reaction Time, hr | Total mmol Gases Collected | Composition of Gas |
|---|---|---|---|
| A | 0.5 | 0.263 | — |
|  | 2.0 | 0.476 | Hydrogen, 99.2%; Methane, nil |
| B | 19.0 | 0.720 | — |
|  | 24.0 | 0.804 | Hydrogen, 99.1%; Methane, 0.5% |

EXAMPLE 3

PhSiH$_3$, 326 mg (3.0 mmol) and Cp*$_2$LuMe, 46 mg (0.1 mmol and cyclohexane solvent, 2 ml, were combined in a reaction vessel under a very slow purge of dry nitrogen gas. After intervals of 0.25, 0.5, 1.0, 3.0, 6.0, and 72 hr, 50 $\mu$l aliquots were removed from the reaction mixture and added to 1 ml of tetrahydrofuran in septum-sealed vials. Analysis of the samples by GPC showed ca. 95% conversion of PhSiH$_3$ within 0.25 hr and the appearance of higher molecular weight oligomers. The distribution of oligomers changed with time, showing up to eight resolved peaks over 6 hr with higher molecular weight peaks increasing relative to lower molecular weight peaks over time. The molecular weight values relative to polystyrene determined for peaks in the gel permeation chromatography traces show increments of 70–80 molecular weight units from peak to peak, consistent with the formation of oligomers H(PhSiH)$_n$H with n=0–5 after 1 hr and n=−>8 after 6 hr. GC/MS results on the samples were consistent with the presence of species with n=at least up to 5 after 6 hr.

EXAMPLE 4

Samples prepared as in Example 3 were stirred for longer than one day and gradually a white precipitate formed, the amount increasing with time. The white precipitate was collected by filtration and dried. The 1H NMR showed a singlet Si—H peak at 4.64 ppm and phenyl resonances centered at 7.13, 7.18, 7.39 in THF-d$_8$. High resolution MS of the material showed a parent ion at m/e = 636.143 (calc for C$_{36}$H$_{36}$Si$_6$ 636.123). Thus the compound is identified as the all-trans isomer of the cyclic polysilane [Si(C$_6$H$_5$)H]$_6$.

EXAMPLE 5.

About 25 mg (0.04 mmol) of Cp*$_2$LaCH(SiMe$_3$)$_2$ was added to 2 ml of PhSiH$_3$ to give a clear solution. Heating to about 40° C. initiated gas evolution which then continued without further heating. After 2 hr gas was still evolving, and the solution was viscous. The $^1$H NMR spectrum of the product mixture in $C_6D_{12}$ contained resonances characteristic of $H(PhSiH)_nH$.

EXAMPLE 6

About 20 mg (0.04 mmol) of Cp*$_2$YCH(SiMe$_3$)$_2$ was dissolved in 1 ml of PhSiH$_3$. After the mixture was heated briefly to about 40° C., evolution of hydrogen and formation of H(PhSiH)nH commenced. The solution became quite viscous after 30 min.

EXAMPLE 7

About 20 mg (0.03 mmol) of Cp*$_2$SmCH(SiMe$_3$)$_2$ was dissolved in 1 ml of PhSiH$_3$. After the mixture was heated briefly, evolution of hydrogen and formation of $H(PhSiH)_nH$ commenced (seen by NMR).

In Examples 8–12, the catalyst and solvent were combined in a glass tube under nitrogen. At the temperature of liquid nitrogen, the tube was evacuated, and alkyl silane gas was condensed in. The flask was closed with an o-ring stopcock, and heated at an elevated temperature with stirring. The term "non-condensible gases" refers to gases that have an appreciable vapor pressure at the temperature of liquid nitrogen. "Condensible gases" refers to gases that do not have an appreciable vapor pressure at this temperature.

EXAMPLE 8

A mixture of 0.052 g (0.11 mmol) of Cp*$_2$LuMe and 14.7 mmol of MeSiH$_3$ in 3 ml of cyclohexane was heated at 70° C. Periodically, non-condensible product gases consisting of mixtures of hydrogen and methane were removed from the reactor and measured. The quantity of these gases produced after 163 hr at reaction temperature was 1.3 mol/mol of MeSiH$_3$ converted to polymer.

| Time at Reaction Temp., hr | Gases Formed, mmol (Cumulative Sum) |
| --- | --- |
| 1 | 3.79 |
| 2 | 5.72 |
| 4 | 7.34 |
| 9 | 9.69 |
| 25 | 12.08 |
| 163 | 16.13 |

After evaporation of condensible gases and solvent from the product mixture, a brittle polymeric solid, 0.53 g, was isolated.

Anal. Found: C, 24.2; H. 7.04; Si, 64.8; Lu, 3.82%. Found: $M_w$ 1660; $M_n$ 1040 [using a 500 Å Ultrastyra ® size exclusion liquid chromatography column (Waters Co.) eluted with tetrahydrofuran; polystyrene reference].

$^1$H NMR, THF−d$_8$, 3.9 (SiH, broad, 1.45 H) 2.01 (C$_5$Me$_5$) 0.41 (SiMe, broad, 3H) ppm. $^{13}$C NMR, THF−d$_8$, 118.57 (C$_5$Me$_5$) 12.4, 12.8 (C$_5$Me$_5$) 7.3 (broad, SiMe) ppm. $^{29}$Si NMR, THF−d$_8$, −33.4 (SiH$_2$, sharp) −53, −66 (SiH, broad) −61 (SiH$_2$, broad) ppm.

EXAMPLE 9

A mixture of 0.104 g (0.226 mmol) of Cp*$_2$LuMe and 29.8 mmol of MeSiH$_3$ in 6 ml of cyclohexane was heated 6.7 hr at 70° C. Non-condensible gases were removed from the reaction mixture, and heating at 70° C. was continued 18 hr. After removal of gases and evaporation of solvent from the product mixture, a tough polymer, 0.92 g, was isolated. At ambient temperature, fibers ca. 1 cm in length and 1 mm in diameter were pulled from the product. Found: $M_w$ 1020; $M_n$ 469 [using a series of 500 Å, 100 Å, and 50 Å Phenogel ® size exclusion liquid chromatography columns (Phenomenex Co.) eluted with tetrahydrofuran; polystyrene reference].

EXAMPLE 10

A mixture of 0.104 g (0.226 mmol) of Cp*$_2$LuMe and 30.1 mmol of MeSiH$_3$ in 6 ml of cyclohexane was heated 6 hr at 70° C. Non-condensible gases, 14.4 mmol, were removed from the reaction mixture, and heating at 70° C. was continued for 18 hr. After removal of non-condensible gases, 8.4 mmol, and evaporation of volatile products and solvent, a polymer, 0.82 g, remained from which thin fibers, 8 cm, were pulled.

Found: $M_w$ 763; $M_n$ 354 [using a series of 500 Å, 100 Å, and 50 Å Phenogel ® size exclusion liquid chromatography columns (Phenomenex Co.) eluted with tetrahydrofuran; polystyrene reference].

EXAMPLE 11

A mixture of 0.104 g (0.226 mmol) of Cp*$_2$LuMe and 30.1 mmol of MeSiH$_3$ in 6 ml of cyclohexane was heated 15 hr at 63–70° C. After removal of non-condensible gases, 13.9 mmol, and evaporation of volatile products and solvent, a polymer remained, 0.51 g, from which thin fibers, 20 cm, were pulled.

Found: $M_w$ 742; $M_n$ 323 [using a series of 500 Å, 100 Å, and 50 Å Phenogel ® size exclusion liquid chromatography columns (Phenomenex Co.) eluted with tetrahydrofuran; polystyrene reference].

EXAMPLE 12

A mixture of 0.052 g (0.113 mmol) of Cp*$_2$LuMe and 2.77 mmol of Me$_2$SiH$_2$ in 2 ml of cyclohexane was heated at 130° C. Periodically, non-condensible product gases consisting of mixtures of hydrogen and methane were removed from the reactor and measured. The quantity of these gases produced after 158 hr at reaction temperature was 1.4 mol/mol of Me$_2$SiH$_2$ converted to polymer.

| Time at Reaction Temp., hr | Gases Formed, mmol (Cumulative Sum) |
| --- | --- |
| 65 | 1.42 |
| 94 | 1.54 |
| 158 | 1.72 |

After evaporation of condensible gases and solvent from the product mixture, a brittle polymeric solid 0.107 g, was isolated.

Anal. Found: C, 43.8; H, 6.9; Si, 28.6%.

EXAMPLE 13

A 0.205 g portion of the polysilane made in Example 8 was heated under vacuum in an open boron nitride container housed within a silica tube. The temperature of the assembly was increased from ambient to 800° C. at a rate of 5° C./min and was held at 800° C. for 2 hr. The weight of the dark gray product was 0.165 g.

Anal. Found: C, 22.1; Si, 71.6; Lu, 4.66%. The analysis corresponds to a composition SiC$_{0.72}$LuO$_{0.01}$. A portion of the SiC$_{0.72}$Lu$_{0.01}$ composition was heated 1 hr at 1400° C. under argon. The X-ray powder pattern of the product was that of a mixture of SiC and elemental Si.

EXAMPLE 14

PhSiH$_3$, 0.551 g (1 equiv, 5.1 mmol) and 1,5-hexadiene, 0.414 g (1 equiv, 5.1 mmol) were dissolved in pentane (2 ml). This solution was added dropwise to a stirred solution of Cp*$_2$LuMe, 37 mg (0.08 mmol) in pentane (5 ml). After 30 min the solution was evaporated at 0° C. to give essentially quantiative yield of a colorless oily residue. The residue was characterized as PhSiH$_2$[CH$_2$(C$_5$H$_9$)] by $^1$H NMR [in THF—d$_8$: 7.298, 7.551 (phenyl, 3H and 2H) 4.35 (SiH, 2H) 1.044, 1.136, 1.5, 1.624, 1.82, 1.919 (methylcyclopentyl group; 2H, 2H, 2H, 2H, 1H respectively)] and $^{13}$C NMR [17.73 (SiCH$_2$) 25.84, 36.3 (cyclopentyl CH$_2$s) 37.94 (cyclopentyl CH) 128.6, 130.4, 133.36, 136.1 (phenyl)] and CG-MS (DB−1 3M 75-290/10 deg per min) room temperature=3.8 min, m/e=190.1173 (calc for C$_{12}$H$_{18}$Si 190.1178).

When the same reaction as above was carried out, but with PhSiH$_3$ (1 equiv) and 1,5-hexadiene (2 equiv), the doubly alkylated product PhSiH[CH$_2$(C$_5$H$_9$)]$_2$ was obtained. PhSiH[CH$_2$(C$_5$H$_9$)]$_2$ was also characterized by $^1$H [in THF—d$_8$: 7.297, 7.53 (phenyl, 3H and 2H) 4.39 (SiH, 1H) 1.83, 1.603, 1.49, 1.09 and 0.98 (two methylcyclopentyl groups, (2+4)H, 4H, 4H, 4H, 4H respectively] and 13C NMR [in THF—d$_8$: 20.6 (SiCH$_2$) 25.92. 36.7 (cyclopentyl CH$_2$ carbons) 37.83 (cyclopentyl CH) 128.6, 129.88, 135.5, 137.3 (phenyl)] and GC-MS(DB-1 3M 75-290/10 deg per min) rt=9.9 min, m/e=b 272.1947 (calc for C$_{18}$H$_{28}$Si 272.1960).

EXAMPLE 15

PhSiH$_3$, 0.556 g (1 equiv, 5.1 mmol) and 3,3-dimethyl-1-butene, 0.414 g (1 equiv, 5.0 mmol) were dissolved in pentane (2 ml). This solution was added dropwise to a stirred solution of Cp*$_2$LuMe, 37 mg (0.08 mmol) in pentane (5 ml). After 30 min the solution was evaporated at 0° C. to give essentially quantiative yield of a colorless oily residue. The residue was characterized as PhSiH$_2$[CH$_2$CH$_2$CMe$_3$] by $^1$H NMR [in THF—d$_8$: 7.53, 7.30 (phenyl; 2H,3H ) 4.30 (SiH, 2H) 1.32 (CH$_2$, 2H) 0.86 (SiCH$_2$ and CMe$_3$ overlapping, 11H)] and $^{13}$C NMR [in THF—d$_8$: 5.44 (SiCH$_2$) 29.35 (3Me) 32.01 (tertiary C) 40.24 (CH$_2$) 128.8, 130.36, 133.2, 135.98 (phenyl)].

When the same reaction as above was carried out, but with PhSiH$_3$ (1 equiv) and 3,3-dimethyl-1-butene (2 equiv), the doubly alkylated product PhSiH[CH$_2$CH$_2$CMe$_3$]$_2$ was obtained. PhSiH[CH$_2$CH$_2$CMe$_3$]$_2$ was also characterized by $^1$H [in THF—d$_8$: 0.801 (SiCH$_2$, 4H) 0.874 (Me, 18H) 1.28 (CH$_2$, 4H) 4.29 (SiH, 1H) 7.3, 7.5 (phenyl; 2H, 3H)] and $^{13}$C NMR [in THF—d$_8$: 7.04 (SiCH$_2$) 29.4 (6Me) 31.95 (tertiary C) 39.54 (CH2) 128.98, 135.44, 133.2, 136.53 (phenyl)].

EXAMPLE 16

PhSiH$_3$, 0.84 g (1 equiv. 0.77 mmol) and 3,3- dimethyl-1butene, 0.065 g (1 equiv. 0.8 mmol) were dissolved in C$_6$D$_6$ (0.4 ml). Cp*$_2$SmCH(SiMe$_3$)2, 11 mg (0.019 mmol) was added. After 1 hr the solution was examined by $^1$H NMR. The product, PhSiH$_2$[CH$_2$CH$_2$CMe$_3$], was observed in the $^1$H NMR spectrum at 7.55, 7.21 (phenyl; 2H, 3H) 4.52 (SiH, 2H) 1.32 (CH$_2$, 2H) 0.85 (SiCH$_2$ and CMe$_3$ overlapping, 11H)].

EXAMPLE 17

PhSiH$_3$, 0.84 g (1 equiv, 0.77 mmol) and 3,3-dimethyl-1-butene, 0.065 g (1 equiv, 0.88 mmol) were dissolved in C$_6$D$_6$ (0.4 ml). Cp*$_2$LaCH(SiMe$_3$)$_2$, 10 mg (0.019 mmol) was added. After 1 hr the solution was examined by $^1$H NMR. The product, PhSiH$_2$[CH$_2$CH$_2$CMe$_3$], was observed in the $^1$H NMR spectrum at 7.55, 7.21 (phenyl; 2H, 3H) 4.52 (SiH, 2H) 1.32 (CH$_2$, 2H) 0.85 (SiCH$_2$ and CMe$_3$ overlapping, 11H)].

EXAMPLE 18

PhSiH$_3$, 0.84 g (1 equiv, 0.77 mmol) and 3,3- eimethyl-1-butene, 0.065 g (1 equiv, 0.8 mmol) were dissolved in C$_6$D$_6$ (0.4 ml). Cp*$_2$YbMe.(diethyl ether), 10 mg (0.019 mmol) was added. After 1 hr the solution was examined by $^1$H NMR. The product, PhSiH$_2$[CH$_2$CH$_2$CMe$_3$], was observed in the $^1$H NMR spectrum at 7.55, 7.23 (phenyl; 2H, 3H) 4.58 (SiH, 2H) 132 (CH$_2$, 2H) 0.86 (SiCH$_2$ and CMe$_3$ overlapping, 11H)].

We claim:

1. A process for the production of polysilanes comprising contacting a silane of the formula R$^1$R$^8$SiH$_2$ with a compound of the formula Cp$_2$MR$^2$ wherein:

R$^1$ is hydrogen, saturated hydrocarbyl or aromatic hydrocarbyl;

R$^8$ is hydrogen, saturated hydrocarbyl or aromatic hydrocarbyl;

Cp is $\eta^5$-cyclopentadienyl or $\eta^5$-cyclopentadienyl substituted with hydrocarbyl, substituted hydrocarbyl or silyl;

M is scandium, yttrium or a rare earth metal; and

R$_2$ is saturated or aromatic hydrocarbyl, substituted saturated hydrocarbyl, substituted aromatic hydrocarbyl, hydrogen or silyl.

2. The process as recited in claim 1 wherein said R$^8$ of the silane of formula RR$^8$SiH$_2$ is hydrogen or methyl.

3. The process as recited in claim 2 wherein said R$^1$ of the silane of formula R$^1$R$^8$SiH$_2$ is alkyl containing less than 6 carbon atoms, or aryl.

4. The process as recited in claim 3 wherein said R$^1$ of formula R$^1$R$^8$SiH$_2$ is methyl, ethyl or phenyl.

5. The process as recited in claim 4 wherein R$^1$R$^8$SiH$_2$ is phenylsilane.

6. The process as recited in claim wherein said Cp of the formula Cp$_2$MR$^2$ is $\eta^5$-cyclopentadienyl or $\eta^5$pentamethylcyclopentadienyl.

7. The process as recited in claim 1 wherein said R$^2$ group of formula Cp$_2$MR$^2$ is hydrogen, phenyl or bis(-trimethylsilyl)methyl.

8. The process as recited in claim 7 wherein said R$^2$ group of formula Cp$_2$MR$^2$ is an alkyl group containing less than 6 carbon atoms, or hydrogen.

9. The process as recited in claim 8 wherein said R$^2$ group is methyl, or hydrogen.

10. The process as recited in claim 1 wherein said M of formula Cp$_2$MR$^2$ is yttrium, lanthanum, samarium or lutetium.

11. The process as recited in claim 10 wherein said M of formula Cp$_2$MR$^2$ is lutetium.

12. The process as recited in claim 11 wherein Cp$_2$MR$^2$ is bis($\eta^5$-pentamethylcyclopentadienyl)methyl lutetium.

13. The process as recited in claim 1 wherein the molar ratio of said silane to said Cp$_2$MR$^2$ is from about 30:1 to about 10,000:1.

14. The process as recited in claim 13 wherein said ratio is from about 100:1 to about 1,000:1.

15. The process as recited in claim 1 wherein the temperature is from about −30° C. to about 250° C.

16. The process as recited in claim 15 wherein the temperature is from about 0° C. to about 150° C.

17. The process as recited in claim 1 wherein a solvent is present comprising an alkane, cycloalkane or an aromatic hydrocarbon.

18. The process as recited in claim 1 wherein the reaction mass is agitated.

19. The process as recited in claim 1 carried out under an inert atmosphere.

20. The process as recited in claim 1 carried out at a pressure above atmospheric pressure.

21. A process for the hydrosilation of alphaolefins comprising contacting an alpha-olefin of the formula $H_2C=CR^3R^4$ with a silane of the formula $R^5R^6SiH_2$ in the presence of a catalyst of the formula $Cp_2MR^2$, wherein:

$R^3$ and $R^4$ are independently hydrocarbyl or substituted hydrocarbyl;

$R^5$ is hydrogen, hydrocarbyl or substituted hydrocarbyl;

$R^6$ is hydrogen, siloxy, hydrocarbyl or substituted hydrocarbyl;

Cp is $\eta^5$-cyclopentadienyl or $\eta^5$-cyclopentadienyl substituted with hydrocarbyl, substituted hydrocarbyl or silyl;

M is scandium, yttrium or a rare earth metal; and $R^2$ aromatic hydrocarbyl, substituted saturated or aromatic hydrocarbyl, hydrogen or silyl.

22. The process as recited in claim 21 wherein said Cp of the catalyst of formula $Cp_2MR^2$ is $\eta^5$cyclopentadienyl or $\eta^5$-pentamethylcyclopentadienyl.

23. The process as recited in claim 21 wherein said $R^2$ of formula group $Cp_2MR^2$ is hydrogen, alkyl, phenyl or bis(trimethylsilyl)methyl.

24. The process as recited in claim 23 wherein said $R^2$ group of formula $Cp_2MR^2$ is methyl, or hydrogen.

25. The process as recited in claim 21 wherein said M of formula $Cp_2MR^2$ is yttrium, lanthanum, samarium or lutetium.

26. The process as recited in claim 25 wherein said M of formula $Cp_2MR^2$ is lutetium.

27. The process as recited in claim 25 wherein $Cp_2MR^2$ is bis($\eta^5$-pentamethylcyclopentadienyl)methyl lutetium.

28. The process as recited in claim 21 wherein said $R^5$ of formula $R^5R^6SiH_2$ is hydrocarbyl, and said $R^6$ is hydrogen.

29. The process as recited in claim 21 wherein said $R^5$ and $R^6$ of the silane of formula $R^5R^6SiH_2$ are each hydrocarbyl.

30. The process as recited in claim 21 wherein said silane is phenylsilane, methylsilane, dimethylsilane or phenylmethylsilane.

31. The process as recited in claim 21 wherein said $R^3$ and $R^4$ of the alpha-olefin of formula $H_2C=CR^3R^4$ are independently each alkyl.

32. The process as recited in claim 21 wherein said $R^3$ of the alpha-olefin of formula $H_2C=CR^3R^4$ is hydrogen and said $R^4$ is alkyl.

33. The process as recited in claim 21 carried out in a solvent.

34. The process as recited in claim 33 wherein said solvent is a hydrocarbon.

35. The process as recited in claim 34 wherein said solvent is an alkane, a cycloalkane or an aromatic hydrocarbon.

36. The process as recited in claim 21 wherein the molar ratio of said silane to said catalyst is from about 30:1 to about 10,000:1.

37. The process as recited in claim 36 wherein said ratio is from about 100:1 to about 1,000:1.

38. The process as recited in claim 21 wherein the temperature is from about $-70°$ C. to about $250°$ C.

39. The process as recited in claim 38 wherein the temperature is from about $-50°$ C. to about $150°$ C.

40. The process as recited in claim 39 wherein the temperature is from about $0°$ C. to about $100°$ C.

41. The process as recited in claim 21 wherein the reaction mass is agitated.

42. The process as recited in claim 21 carried out under an inert atmosphere.

43. The process as recited in claim 21 carried out at a pressure above atmospheric pressure.

* * * * *